US010335285B2

United States Patent
Viscardi et al.

(10) Patent No.: US 10,335,285 B2
(45) Date of Patent: Jul. 2, 2019

(54) REVISEABLE STEMLESS PROSTHESES AND METHODS

(71) Applicant: Howmedica Osteonics Corp., Mahwah, NJ (US)

(72) Inventors: David Viscardi, Glen Rock, NJ (US); Nicholas Olson, Belleville, NJ (US); Jonathan You, Far Hills, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 18 days.

(21) Appl. No.: 15/587,809

(22) Filed: May 5, 2017

(65) Prior Publication Data
US 2018/0104064 A1    Apr. 19, 2018

Related U.S. Application Data

(60) Provisional application No. 62/407,804, filed on Oct. 13, 2016.

(51) Int. Cl.
*A61F 2/40* (2006.01)
*A61B 17/16* (2006.01)
(Continued)

(52) U.S. Cl.
CPC ........ *A61F 2/4014* (2013.01); *A61B 17/1684* (2013.01); *A61B 17/56* (2013.01);
(Continued)

(58) Field of Classification Search
CPC ...... A61F 2/28; A61F 2/30; A61F 2/40; A61F 2/4014
See application file for complete search history.

(56) References Cited

U.S. PATENT DOCUMENTS 3,783,868 A * 1/1974 Bokros ............. A61M 39/0247
424/448
8,152,855 B2   4/2012 Tulkis et al.
(Continued)

FOREIGN PATENT DOCUMENTS

| CA | 1285705 C | 7/1991 |
| WO | 2009049182 A1 | 4/2009 |
| WO | 2012138996 A1 | 10/2012 |

OTHER PUBLICATIONS

Bell, R. et al., "Computer Planning and Intraoperative Navigation for Palatomaxillary and Mandibular Reconstruction with Fibular Free Flaps" Digital Technology and Fibular Free Flaps, Copyright 2011, J. American Association of Oral and Maxillofacial Surgeons, pp. 724-732.
(Continued)

*Primary Examiner* — Jason-Dennis N Stewart
(74) *Attorney, Agent, or Firm* — Lerner, David, Littenberg, Krumholz & Mentlik, LLP

(57) ABSTRACT

Disclosed herein are orthopedic revision systems including a base member having a collar portion and at least one stabilization portion extending outwardly from the collar portion. The systems may further include a stem member having an attachment portion and a shaft portion, the stem member configured to be received at least partially through an opening in the collar portion such that the attachment portion lies adjacent the collar portion and the shaft portion lies adjacent the at least one stabilizing portion. In a method of performing revision surgery with such orthopedic systems includes forming an opening in the collar of the base member for receipt of the stem member by removing an inner portion of the collar portion and inserting the stem member at least partially through the opening in the collar portion such that the attachment portion lies adjacent the
(Continued)

collar portion and the shaft member lies adjacent the at least one stabilizing portion.

18 Claims, 14 Drawing Sheets

(51) Int. Cl.
 *A61B 17/56* (2006.01)
 *A61F 2/46* (2006.01)
 *A61F 2/30* (2006.01)
(52) U.S. Cl.
 CPC .............. *A61F 2/40* (2013.01); *A61F 2/4059* (2013.01); *A61F 2/4612* (2013.01); *A61F 2/4637* (2013.01); *A61F 2/4684* (2013.01); *A61B 2017/564* (2013.01); *A61F 2002/3069* (2013.01); *A61F 2002/30331* (2013.01); *A61F 2002/30604* (2013.01); *A61F 2002/30841* (2013.01); *A61F 2002/4033* (2013.01); *A61F 2002/4074* (2013.01)

(56) References Cited

U.S. PATENT DOCUMENTS

| | | |
|---|---|---|
| 8,512,410 B2 | 8/2013 | Metcalfe et al. |
| 2001/0047210 A1 | 11/2001 | Wolf |
| 2007/0282450 A1* | 12/2007 | Habermeyer ......... A61F 2/4003 623/19.14 |
| 2010/0121458 A1 | 5/2010 | Ledger et al. |
| 2012/0191201 A1 | 7/2012 | Smits et al. |
| 2013/0261754 A1 | 10/2013 | Anthony et al. |
| 2014/0277540 A1 | 9/2014 | Leszko et al. |
| 2014/0379089 A1 | 12/2014 | Bachmaier |

OTHER PUBLICATIONS

Comprehensive Nano Stemless Shoulder Anatomic and Reverse, Surgical Technique, Biomet Orthopedics, 60 pages, 2012.
European Search report for EP application No. 17195211.2 dated Jan. 25, 2018, pp. 1-2.

* cited by examiner

REVISEABLE STEMLESS PROSTHESES AND METHODS

CROSS-REFERENCE PARAGRAPH

The present application claims the benefit of priority to U.S. Provisional Application No. 62/407,804 filed Oct. 13, 2016, which is incorporated herein by reference in its entirety.

FIELD OF THE INVENTION

The present invention relates in general to prostheses that can be used in both primary and revision procedures and in particular to prostheses that can guide the placement of other prosthetic components in a revision procedure.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas, resulting in pain, stiffness, and decreased mobility. The same can happen in cases where tendons in a joint become lax or soft tissues in or adjacent the joint tear becomes damaged or worn.

Arthroplasty procedures can be used to repair such damaged joints. During a typical arthroplasty procedure, an arthritic or otherwise dysfunctional joint can be remodeled or realigned. A prosthesis or prostheses can be implanted to repair the damaged region. Arthroplasty procedures may take place in any of a number of different regions of the body, such as the knees, hips, shoulders, or elbows, for example.

One type of arthroplasty procedure is a shoulder arthroplasty, in which a damaged shoulder joint may be replaced with prosthetic implants. The shoulder joint may have been damaged by, for example, arthritis (e.g., severe osteoarthritis or degenerative arthritis), trauma, or a rare destructive joint disease.

Prostheses that are implanted into a damaged region may provide support and structure to the damaged region, and may help to restore the damaged region, thereby enhancing its functionality. Prior to implantation of a prosthesis in a damaged region, the damaged region may be prepared to receive the prosthesis. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant. Standard alignment instrumentation and/or patient-specific guides may be used for locating a position and orientation to resect the humeral head for proper humeral stem placement.

Accuracy in implant alignment is an important factor to the success of a surgical procedure. A one to two millimeter translational misalignment, or a one to two degree rotational misalignment, may result in imbalanced ligaments, and may thereby significantly affect the outcome of the procedure. For example, implant misalignment may result in intolerable post-surgery pain, and also may prevent the patient from having proper deltoid tension or range of motion.

To achieve accurate implant alignment, prior to treating (e.g., cutting, drilling, reaming, and/or resurfacing) any regions of a bone, it is important to correctly determine the location at which the treatment will take place and how the treatment will be oriented. It is also often preferable to maintain as much of a patient's natural bone stock as possible during such a procedure. Prostheses generally have a certain life expectancy and in certain cases need to be replaced at some point. If one or more prostheses need to be removed and/or replaced in a revision procedure, a large bone void could be left after their removal. In certain cases, this bone void is not ideal for receipt of revision components. While bone cement can be added to the void to fill space and/or secure revision components, it is generally not a preferred option. Preserving natural bone stock may be vital for the ability to even perform a revision procedure. There exists a need for maintaining the stability and/or positioning of primary components in a revision procedure.

BRIEF SUMMARY OF THE INVENTION

Stemless prostheses or implants generally represent a great option for primary surgeries in younger patients with satisfactory bone stock. Based on the younger patient population that stemless implants are generally implanted in, there is an increased possibility that a revision surgery will be needed for these patients at some point. Reverse shoulder arthroplasty is a popular option for revision surgeries due to the potential for rotator cuff tear arthropathy in older patients. A patient with a stemless implant who has rotator cuff tear arthropathy may need a revision of their humeral component to accommodate a reverse shoulder. Removal of a well fixed humeral stemless prosthesis may cause unnecessary removal of humeral bone and/or a large bone void. The present invention includes the ability to leave a portion of a well fixed humeral stemless implant in place, and implant a stemmed prosthesis in relation to the stemless implant from a prior procedure.

In one embodiment, a stemless humeral implant with certain design features allows for "coring out" a center hole in the implant. The design features in the stemless that allow for coring out include trabecular style metal or "breakaway" metal sections that can be disconnected or mechanically separated intraoperatively. Once disconnected, the center hole of the stemless implant is present as well as a hole in the center of the humeral canal. This hole allows a stem to be at least partially inserted into it. The remaining stemless implant preferably has features that interface with the stem and create a resultant combined implant.

The portion of the stemless implant left in place may be used to position the stem inserted into it. Instead of removing the entire stemless implant and leaving a large void in the bone, the portion of the stemless implant left in place acts as a void filler. Implants used to fill voids in bone in either primary or revision procedures are disclosed in U.S. Pat. Pub. Nos. 2014/0277567 and 2016/0199187, the disclosures of which are hereby incorporated by reference herein in their entireties.

In another embodiment, the cored out hole allows a stem to be implanted within the hole or void and provide clearance for a more distally positioned stem to be implanted into the humerus. A benefit of either option is that the peripheral or flange portion of the stemless implants does not have to be removed resulting in a significant proximal bone defect.

A first aspect of the present invention is an orthopedic revision system comprising a base member having a collar portion and at least one stabilization portion extending outwardly from the collar portion; and a stem member having an attachment portion and a shaft portion, wherein the stem member is configured to be received at least partially through an opening in the collar portion such that the attachment portion lies adjacent the collar portion and the shaft portion lies adjacent the at least one stabilizing portion.

In one embodiment of this first aspect, the collar portion and the at least one stabilization portion of the base member include open cylindrical shafts.

In another embodiment of this first aspect, the collar portion extends in a direction transverse to the at least one stabilization portion. The collar portion and the at least one stabilization portion may intersect to define a corner adapted to lie adjacent to an edge of a medullary canal of a patient's bone.

In yet another embodiment of this first aspect, the base member has an initial configuration and a revision configuration, the collar portion being closed in the initial configuration and defining an opening in the revision configuration. An inner portion of the collar portion may be removed to convert the collar portion from the initial configuration to the revision configuration.

In still yet another embodiment of this first aspect, the stem member includes a ledge portion configured to contact and lay adjacent to the collar portion of the base member when the stem member is operatively coupled to the base member.

In still yet another embodiment of this first aspect, the attachment portion of the stem member defines an engagement portion for insertion into a recess of an articulation member to operatively couple the stem member to the articulation member.

In still yet another embodiment of this first aspect, the attachment portion defines a recess for receipt of an engagement portion of an articulation member to operatively couple the stem member to the articulation member.

A second aspect of the present invention is an orthopedic revision system comprising a base member having a revision configuration including a collar portion and at least one stabilization portion extending outwardly from the collar portion in a direction transverse from the collar portion; and a stem member having an attachment portion and a shaft portion, wherein the stem member is configured to be received at least partially through an opening in the collar portion such that the attachment portion lies adjacent the collar portion and the shaft portion lies adjacent the at least one stabilizing portion.

In one embodiment of this second aspect, the collar portion and the at least one stabilization portion of the base member include open cylindrical shafts.

In another embodiment of this second aspect, the collar portion extends in a direction transverse to the at least one stabilization portion. The collar portion and the at least one stabilization portion may intersect to define a corner adapted to lie adjacent to an edge of a medullary canal of a patient's bone.

In yet another embodiment of this second aspect, the base member has an initial configuration and the revision configuration, the collar portion being closed in the initial configuration and defining the opening in the revision configuration.

In still yet another embodiment of this second aspect, an inner portion of the collar portion is removed to convert the collar portion from the initial configuration to the revision configuration.

In still yet another embodiment of this second aspect, the stem member includes a ledge portion configured to contact and lay adjacent to the collar portion of the base member when the stem member is operatively coupled to the base member.

In still yet another embodiment of this second aspect, the attachment portion of the stem member defines an engagement portion for insertion into a recess of an articulation member to operatively couple the stem member to the articulation member.

In still yet another embodiment of this second aspect, the attachment portion defines a recess for receipt of an engagement portion of an articulation member to operatively couple the stem member to the articulation member.

A third aspect of the present invention is a method of performing revision surgery with an orthopedic system including a base member having a collar portion and at least one stabilization portion extending outwardly from the collar portion and a stem member having an attachment portion and a shaft portion, the method comprising: forming an opening in the collar of the base member for receipt of the stem member by removing an inner portion of the collar portion; and inserting the stem member at least partially through the opening in the collar portion such that the attachment portion lies adjacent the collar portion and the shaft member lies adjacent the at least one stabilizing portion.

In one embodiment of this third aspect, the base member has an initial configuration and a revision configuration, the collar portion being closed in the initial configuration and having the opening formed in the revision configuration.

BRIEF DESCRIPTION OF THE DRAWINGS

Other objects and advantages of the present invention will be apparent from the following detailed description of the present preferred embodiments, which description should be considered in conjunction with the accompanying drawings in which like reference indicate similar elements and in which.

DETAILED DESCRIPTION

Figure 1:
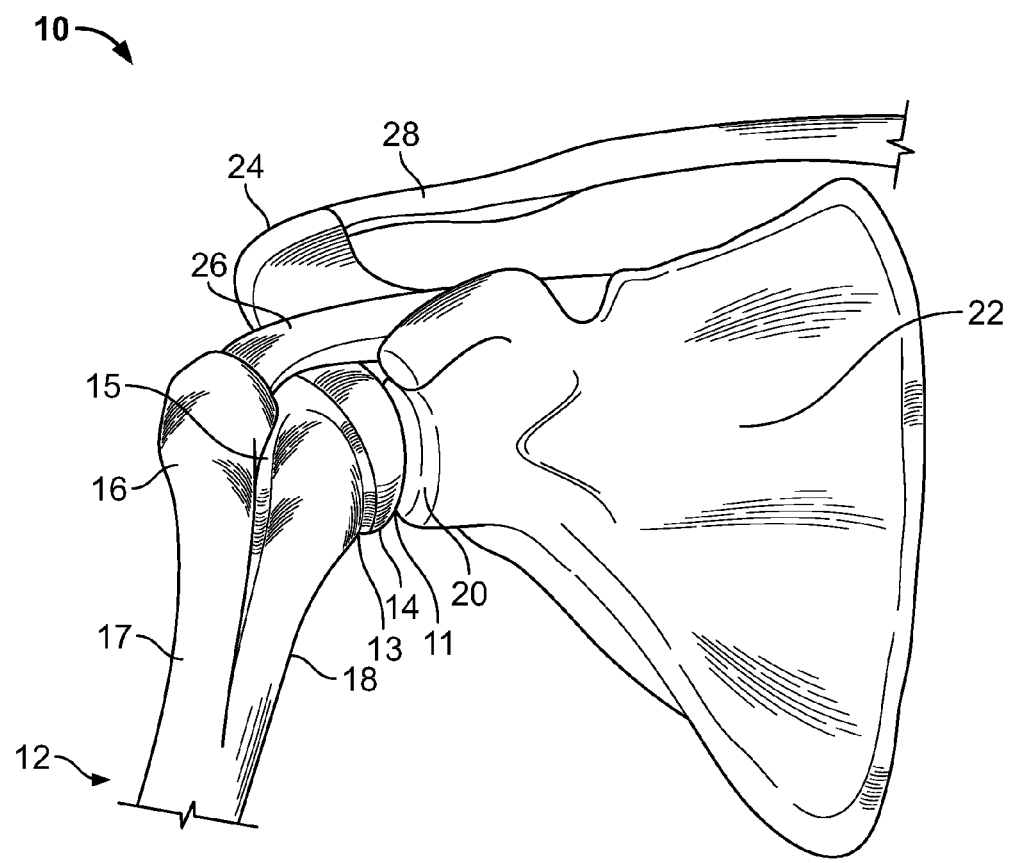
FIG. 1 shows the general shoulder joint anatomy of a patient.
Figure 2:
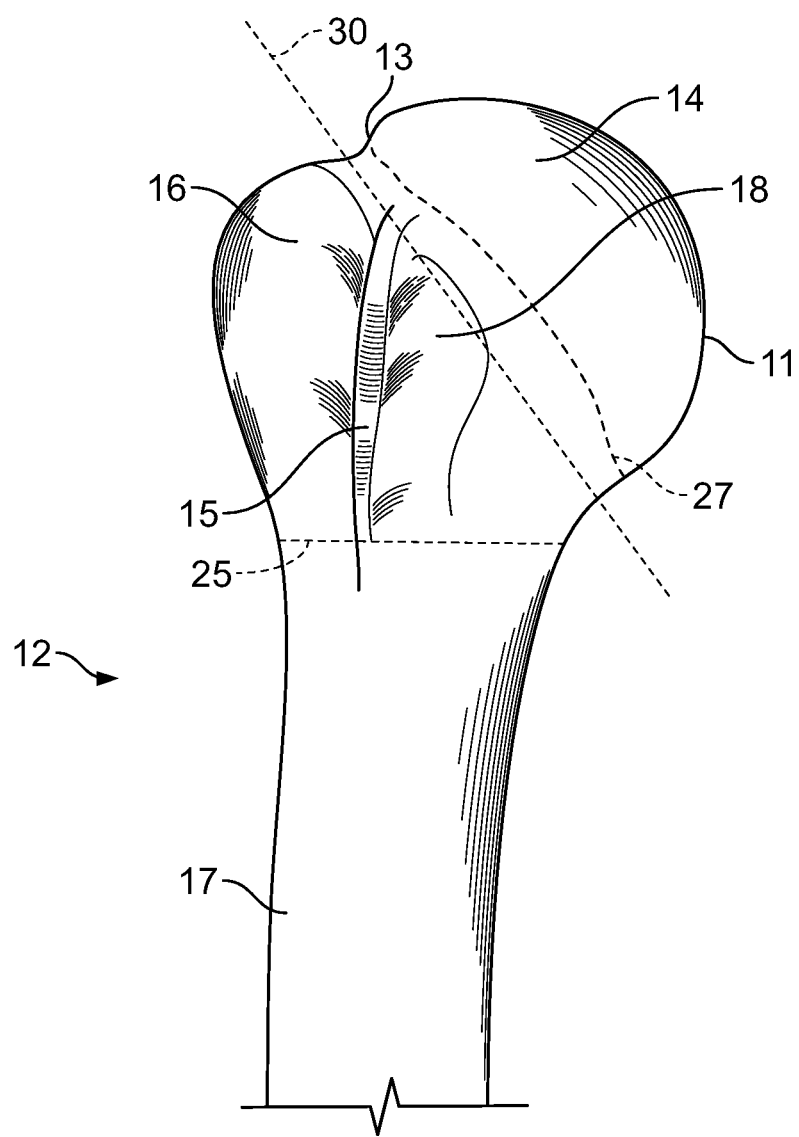
FIG. 2 is a posterior view of a proximal portion of a humerus of the shoulder joint showing a resection line adjacent the anatomical neck of a humerus.

FIG. 1 shows the general anatomy of shoulder joint 10 of a patient. Humerus 12 of joint 10 includes a neck portion 13, a head portion 14 and a shaft portion 17 having a greater tuberosity 16 and a lesser tuberosity 18. Between greater and lesser tuberosities 16, 18 is bicipital groove 15. As shown in FIGS. 1-2, scapula 22 terminates at glenoid 20 having a cavity 21 in which an outer surface 11 of head portion 14 rotates within. Along with humerus 12 and scapula 22, the acromion 24, rotator cuff 26 and clavicle 28 all provide support to the range of motion of the shoulder joint 10 of the patient.

FIG. 2 is a posterior view of a proximal portion of humerus 12 of shoulder joint 10. Head portion 14 includes outer surface 11. Also shown is bicipital groove 15, a substantially straight surcical neck line 25 and a curvy anatomical neck line 27. Outer surface 11, biciptal groove 15, substantially straight surcical neck line 25 and curvy anatomical neck line 27 are all anatomical features of humerus 12 that can be used to aid in determining a resection line 30 and positioning of one or more prosthesis.

Prior to a total shoulder arthroplasty procedure being conducted, shoulder joint 10 is generally compromised through injury or general wear and tear. A compromised joint generally leads to range of motion difficulty and pain for the patient. In a joint 10 that is compromised, head portion 14 and/or glenoid cavity 21 may be degenerated such that the axis of rotation of the shoulder joint is not in the same location as it was prior to joint 10 being compromised.

The axis of rotation of the shoulder joint varies based upon the type of motion. For flexion and extension, the axis of rotation is a transverse axis though the center of the humeral head. For abduction and adduction, the axis of rotation is a sagittal axis thought the center of the humeral head. For internal and external rotation, the axis of rotation is a vertical axis though the center of the humeral head.

During a total shoulder arthroplasty procedure, the humerus is resected in order to receive a humeral stem component. In such a procedure, the humeral head is generally resected and the shaft of the humerus is reamed to receive the humeral stem component prosthesis. It is important that the humeral stem component be positioned in the correct location and orientation in order to restore the axis of rotation of joint 10. Some humeral stem components may include a flange that is adapted to contact a flat portion of resected bone of the humerus in order to correctly position and stabilize the humeral stem component within shaft 17 of humerus 12 such that the axis of rotation of joint 10 may be restored.

Also during a total shoulder arthroplasty procedure, the glenoid is resected in order to receive a glenoid component. In a shoulder arthroplasty procedure for implanting a reverse shoulder prosthesis, a cavity of the glenoid may be reamed and a guide hole may be drilled in order to receive a central screw extending outwardly from an outer contact surface of the glenoid component. The location and orientation of the guide hole may be based on the shape of the glenoid component, for example, such that the glenoid component can be implanted in the resected glenoid cavity and the axis of rotation of the joint may be restored. It is important that the glenoid component be positioned in the correct location and orientation in order to restore the axis of rotation of joint 10. The glenoid component preferably has an articular surface corresponding to an outer surface of a humeral head component which is engaged to the humeral stem component implanted at least partially within the shaft of the humerus. Generally, the glenoid component has a diameter that is approximately 6 mm in diameter larger than the humeral stem component.

Figure 3:
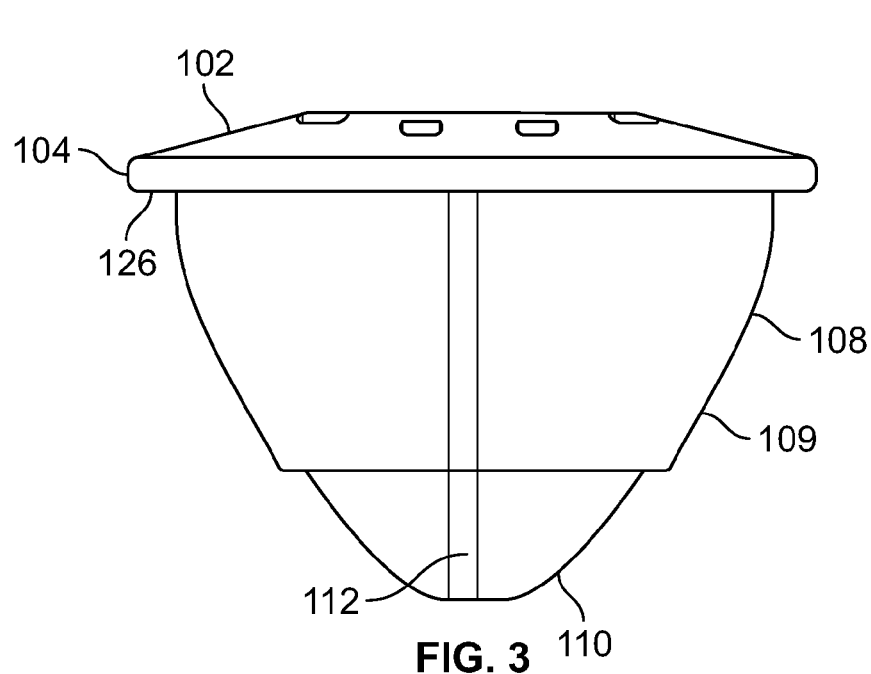
FIG. 3 is a side view of an exemplary stemless prosthesis.

Humerus 12 must therefore be resected at a correct location and orientation in order for a corresponding stemless prosthesis or stem prosthesis to be accurately implanted in shaft 17 of humerus 12 such that the axis of rotation of the shoulder joint may be restored. Thus, the location and orientation of resection line 30, as shown in FIG. 2, is either preoperatively or intraoperatively planned according to one aspect of the present invention. Resection line 30 corresponds to the location and orientation of a stemless implant 100 as shown in FIG. 3.

Figure 4:
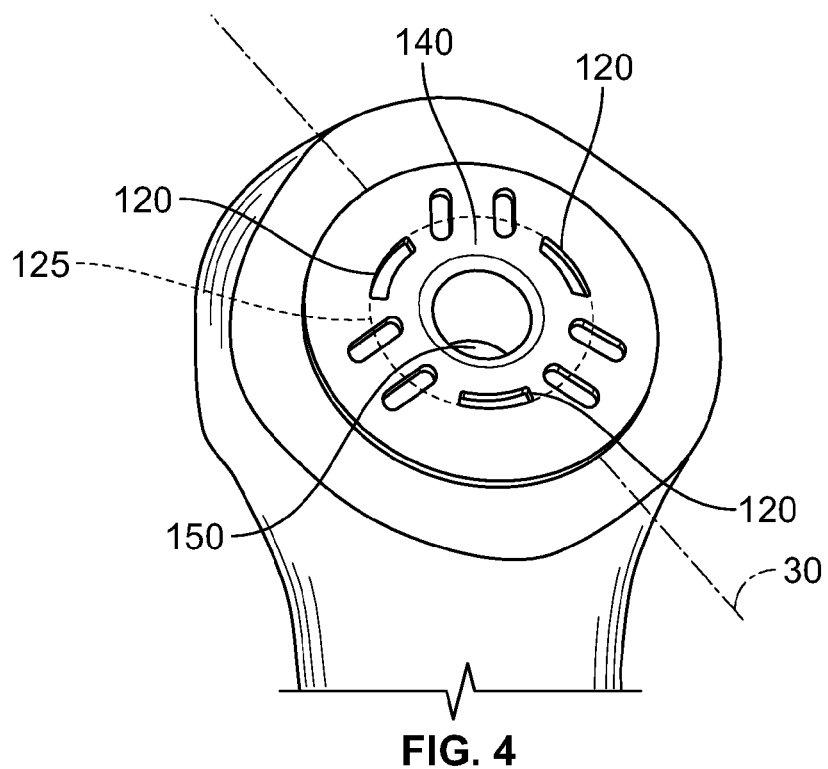
FIG. 4 is a perspective view of the stemless prosthesis shown in FIG. 3 received at least partially within a resected humeral bone.

Stemless implant 100 has an outer or proximal end surface 102, a side flange surface 104, an inner flange surface 106. Outer surface 102 can be planar, sloped or curved. A stabilizing portion 109 of stemless implant 100 includes an engagement body surface 108 and a distal portion 110. Extending from engagement body surface 108 and/or distal portion 110 are one or more protrusions or barbs 112. The protrusions or barbs 112 are present to aid in the stabilization of stemless implant 100 with respect to cancellous bone of the humerus. Inner flange surface 106 is adapted to contact and lie adjacent to the resected bone of the humerus about resection line 30. Inner flange surface 106 is preferably planar but can include features that enhance stability such as recesses for bone ingrowth. Engagement body surface 108 and distal portion 110 as well as protrusions or barbs 112 are adapted to contact reamed bone in the canal of the humerus and stabilize stemless implant 100 within the bone as shown in FIG. 4. In some cases, stemless implant 100 may be impacted into cancellous bone that is partially reamed based on the desired fixation of stemless implant 100 with respect to the humeral bone.

FIGS. 5A-5E show another embodiment of a stemless prosthesis having a base 100'. Base 100' generally includes collar 101' and central anchor 140' coupled thereto. Collar 101' may be generally cylindrical or annular and includes a proximal end surface 102', a distal bone-engaging surface 103', and side flange surface 104 extending along the circumference of the collar. Proximal end surface 102' may be flat, but it can also be inclined or sloped in some embodiments. Side flange surface 104' may have a uniform height, measured from distal to proximal ends of side flange surface 104', or the height may be varied along proximal surface 102'. Although shown as generally cylindrical or annular, collar 101' may have other shapes. Anchor 140' is coupled to collar 101' at a first end 141' and extends distally from the collar along a longitudinal axis 135' to a second end 174'. In the illustrated embodiment, anchor 140' is tapered along longitudinal axis 135' so that first end 141' has a relatively large diameter, with the diameter of the anchor generally narrowing toward second end 174' until the anchor terminates in distal tip 175'; however, in some situations it may be appropriate for anchor 140' to be of uniform size throughout and not tapered. Anchor 140' further includes outer wall 142' extending from first end 141 toward distal tip 175'.

Base 100' includes an annular rim 119' positioned within an interior cavity of collar 101'. Rim 119' defines an opening 130' which is adapted to receive an articulating component (not shown) of the stemless implant. In the illustrated example, base 100' may be adapted to couple to a proximal humerus of a patient, with a prosthetic humeral head adapted to couple to the base via opening 130', the prosthetic humeral head intended to articulate with a native or prosthetic glenoid of the shoulder joint. Although rim 119' and opening 130' may have any shape that suitably mates with the corresponding portion of the prosthetic humeral head, in one example a taper such as a Morse taper may be used to lock the prosthetic humeral head to rim 119'. The proximal end of rim 119 may be substantially flush with the proximal surface 102' of collar 101', although in some embodiments it may extend either proximally or distally of proximal surface 102'. In the illustrated embodiment, the opening 130' defined by rim 119' extends from proximal end surface 102' of collar 101' along longitudinal axis 135' to a proximal surface 139' of anchor 140'. From surface 139' to tip 175', anchor 140' may be generally solid, with the exceptions noted below in connection with the flexible portions of outer wall 142'.

Figure 5A:
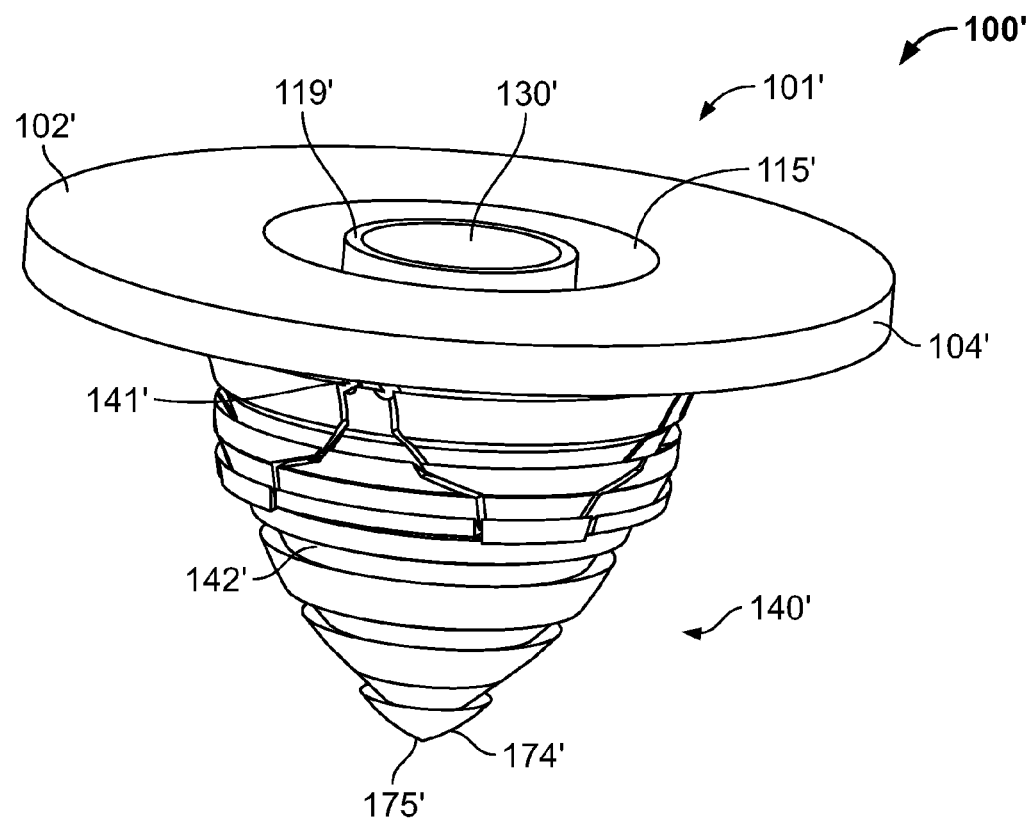
FIG. 5A is a top perspective view of another exemplary stemless prosthesis.
Figure 5B:
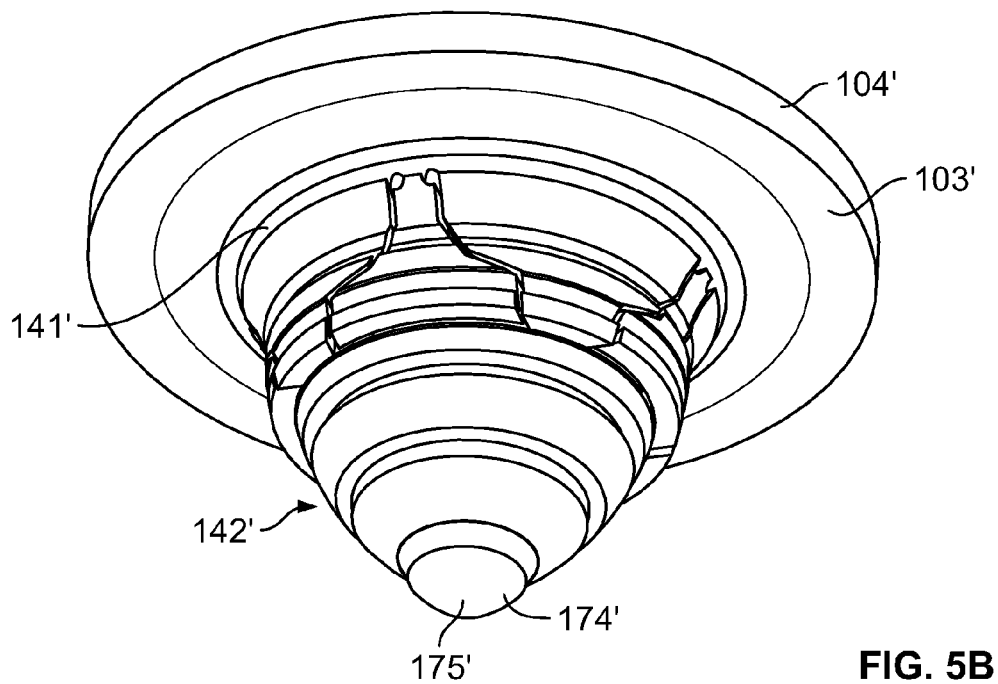
FIG. 5B is a bottom perspective view of the base of FIG. 5A.
Figure 5C:
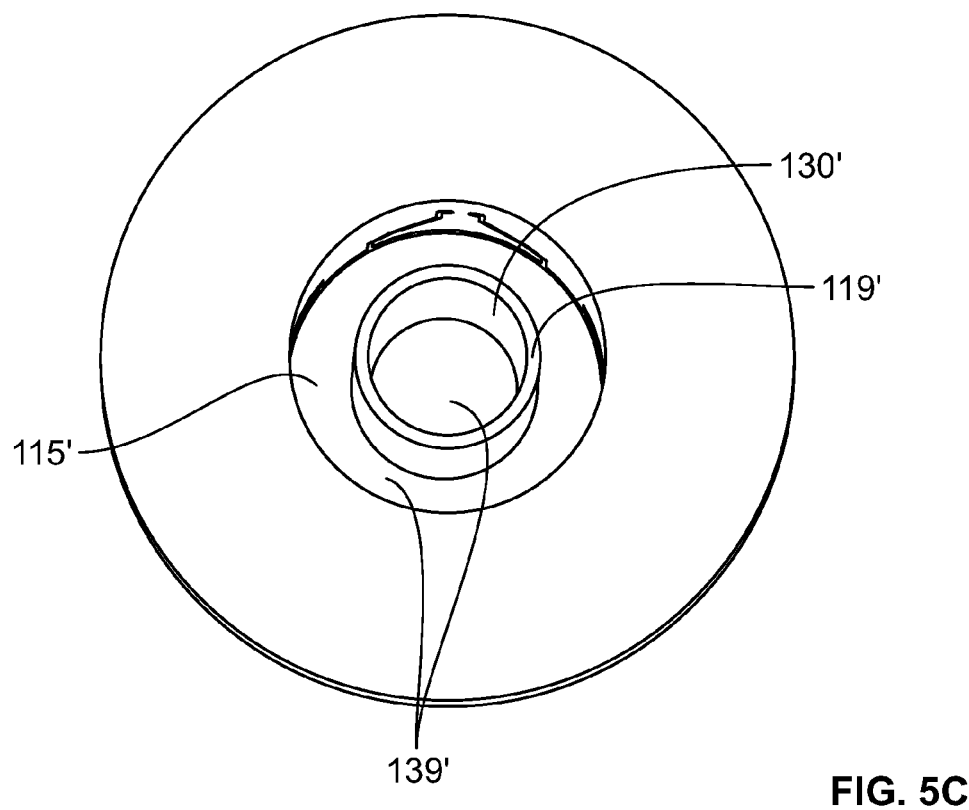
FIG. 5C is a top view of the base of FIG. 5A.
Figure 5D:
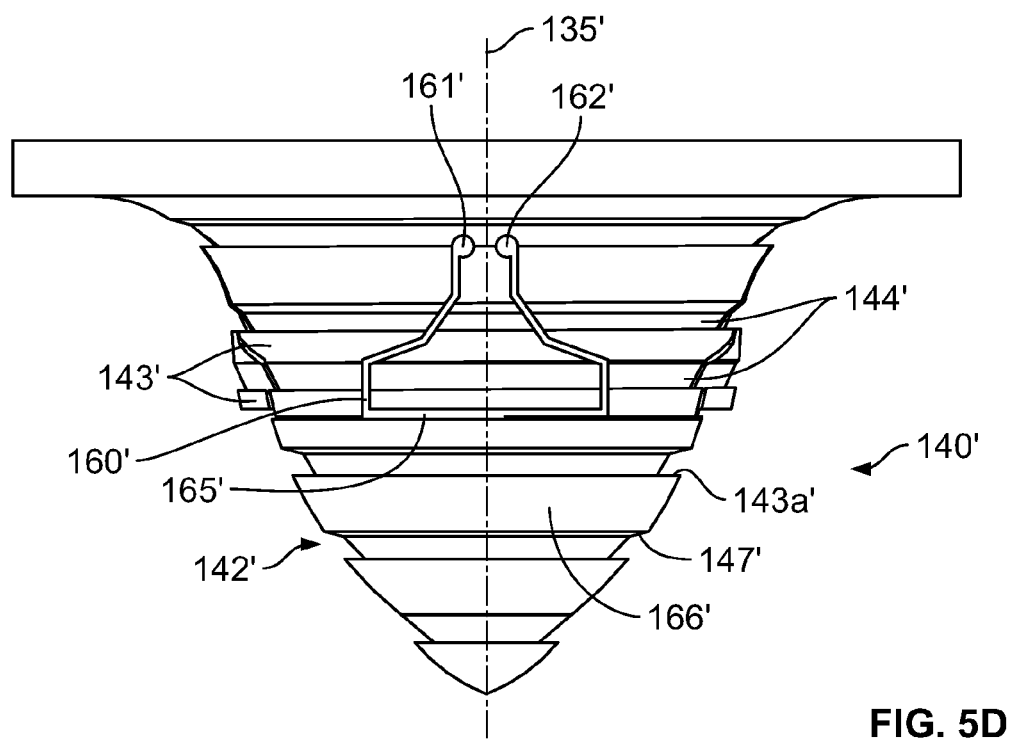
FIG. 5D is a side view of the base of FIG. 5A.

The space between the inner circumference of collar 101' and the outer circumference of rim 119' defines a circular or cylindrical recess 115'. Recess 115' extends from proximal surface 102' distally along longitudinal axis 135' to surface 139'. Rim 119' separates opening 130' and recess 115'. Prior to attaching a prosthetic humeral head to base 100', or after removing a prosthetic humeral head from the base, tools such as insertion and extraction tools may be inserted into opening 130' and/or recess 115', as discussed below FIG. 5D shows a side view of base 100', including outer wall 142' of anchor 140'. Outer wall 142' may have a serrated configuration in which the outer wall includes alternating peaks 143' and troughs 144' in the proximal-to-distal direction, with each peak transitioning into a trough and each trough transitioning into a peak. Peaks 143' and troughs 144' may be disposed substantially circularly around outer wall 142', with the outer surfaces of the peaks and the troughs together defining the outer wall. In other embodiments, peaks 143' and troughs 144' may be disposed helically around outer wall 142' in a screw-like configuration. As noted above, each trough 144' is positioned adjacent to at least one peak 143', and preferably two peaks. Each peak 143' may extend farther radially outward from the longitudinal axis 135' than each adjacent trough 144'. The transition between the outer circumference of each peak 143' to a distally adjacent trough 143' forms a distal surface 147' that is shaped frustoconically.

Although the outer circumferential surface of each peak 143' may be angled along the general contour of anchor 140', each peak may also include a generally curved surface, where a peak transitions into an adjacent trough 144'. With this configuration, the proximal surface of each peak forms a counter support to resist pull-out, torque out, and/or lever out of the base 100' after implantation. For example, in the illustrated embodiment, the transition between the outer circumference of each peak 143' to a proximally adjacent trough 144' forms a hook 143a'. Hook 143a' may extend radially outwardly from adjacent troughs 144' in a proximal-facing hook shape. Hooks 143a' can be advanced into the native bone to fix the anchor to the bone. Once hooks 143a' are engaged in the bone, motion is restricted due to the hooked shape of hooks 143a'.

Figure 5E:
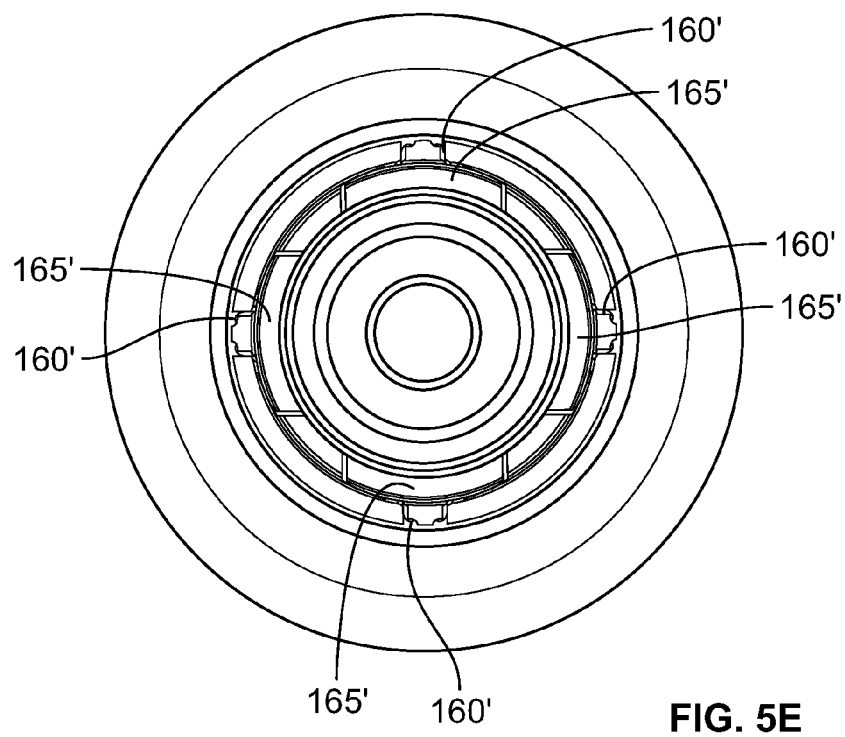
FIG. 5E is a bottom view of the base of FIG. 5A.

FIG. 5D further illustrates a plurality of slots 160' formed in the outer wall 142' of anchor 140'. Slots 160' are designed to enable flexible portions 165' of outer wall 142' to flex and extend radially outwardly of static portions 166'. Each slot 160' may extend through outer wall 142' so that the slot fully extends from the outer surface of the anchor and into recess 115'. Although various methods may be used to create slots 160', in the illustrated embodiment the slot extends from holes 161' and 162' distally to a bottom surface 165' of the slot. Bottom surface 165' may extend around a portion of a circumference of anchor 140' and may be positioned in a plane that is parallel to proximal surface 102' of collar 101' and is coextensive with a plane defined by surface 139'. Holes 161' and 162' may be positioned on proximal portions of outer wall 142' near first end 141'. Holes 161' and 162' may be adjacent to each other but do not overlap, such that a thin connection is maintained between flexible portion 165' and the remainder of outer wall 142'. Although the bottom surface 165' of slot 160' is shown as being disposed through outer wall 142' at an angle generally perpendicular to longitudinal axis 135', the angle may be of varying degrees. As shown in FIG. 5E, base 100' may include four slots 160' that form four flexible portions 165' positioned at substantially equal intervals around the circumference of anchor 140', but it should be understood that more or fewer slots and/or flexible portions may be provided as desired.

Each flexible portion 165, which may be thought of as the portions of outer wall 142' within a particular slot 160', may be biased outwardly from adjacent surfaces of static portion 166' so that, in the absence of applied force, portions of each flexible member extend farther radially outward from longitudinal axis 135' compared to circumferentially adjacent areas of static portion 166'. With this configuration, a tool may be used to pull the flexible portions 165' radially inward to generally align with static portion 166' upon either insertion of base 100' into bone, or extraction of the base out of bone, such that the outer wall 142' of anchor 140' forms a substantially smooth surface. For example, an insertion and/or extraction tool (not shown) may be inserted into opening 130' and/or recess 115' to engage each flexible portion 165' to pull the flexible portions radially inward. This constrained or contracted condition may be referred to as the insertion and/or removal condition. During implantation of base 100', for example into cancellous bone in a prepared proximal humerus, anchor 140' may be driven into the cancellous bone until collar 101' is substantially flush with the proximal humerus. Using a tool to transition base 100' to the insertion condition prior to implantation may provide a substantially smooth surface of the outer wall 142' of anchor 140' to ease the insertion of the base into the bone. Once base 100' is in the desired position in the proximal humerus, the tool may be disengaged from base 100', allowing flexible portions 165' to flex radially outwardly into the bone in which the base is implanted. This condition may be referred to as the implanted or expanded condition. This additional radial force may further aid in achieving suitable fixation of the base 100', despite the base being stemless. Further, during a revision procedure in which base 100' must be removed from the bone, merely pulling the base proximally out of the bone risks trauma due to the flexible portions 165'. Thus, a tool similar or identical to that described above may again be inserted into opening 130' and/or recess 115' and engage each of the flexible portions 16'5 to move them radially inwardly into the removal condition. This transition helps to create clearance between the proximal humerus and the outer wall 142' of anchor 140', particularly at the locations of the flexible portions 165'. In some embodiments, in the absence of applied force, the flexible portions 165' may extend less than about 2 mm or about 3 mm compared to circumferentially aligned areas of static portion 166'. Although this amount of extension may seem small, the radial extension may enable the hooks 143a' associated with the flexible portions 165' to further engage the bone for increased fixation. It should also be understood that the tool used to transition the base from the insertion condition or removal condition to the implanted or expanded condition may be the same tool that is used to hold the base 100' during implantation or explantation, although it may also be a separate tool with no additional function.

FIGS. 6A-6D show a base 200 of a stemless prosthesis according to another embodiment of the disclosure. Base 200 generally includes collar 201 coupled with central anchor 240. Collar 201 may be generally cylindrical or annular and includes a proximal end surface 202, a distal bone engaging-surface 203, and a side flange surface 204. Proximal end surface 202 may be flat as shown, but in other embodiments it may be inclined or sloped. Side flange surface 204 may have a uniform height, the height measured from distal to proximal ends of side flange surface 204, or the height may vary along proximal end surface 202. Although shown as generally cylindrical or annular, collar 201 may have other shapes.

Base 200 includes central anchor 240 coupled to collar 201 at a first end 241 and extending distally from the collar along a longitudinal axis 235 to a second end 274. In the illustrated embodiment, anchor 240 is tapered along longitudinal axis 235 so that first end 241 has a relatively large diameter, with the diameter of the anchor generally narrowing toward second end 274 until the anchor terminates in distal tip 275; although, in some situations it may be appropriate for, anchor 240 to be of uniform size throughout and not tapered.

Figure 6A:
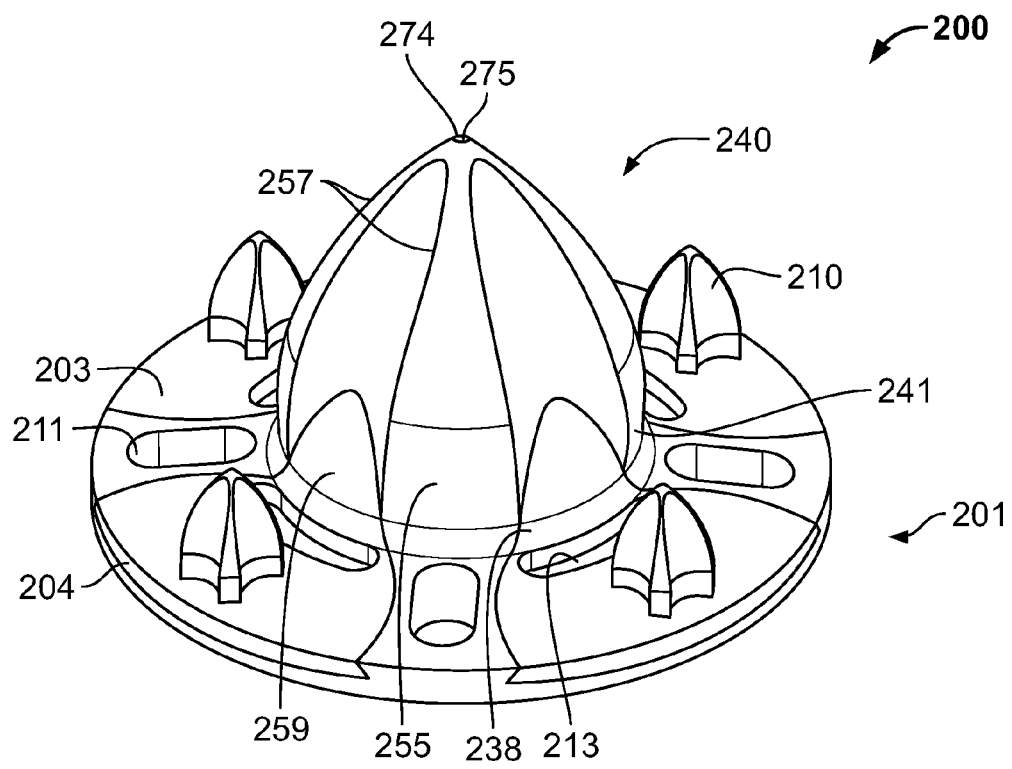
FIG. 6A is a side perspective view of yet another exemplary stemless prosthesis.
Figure 6B:
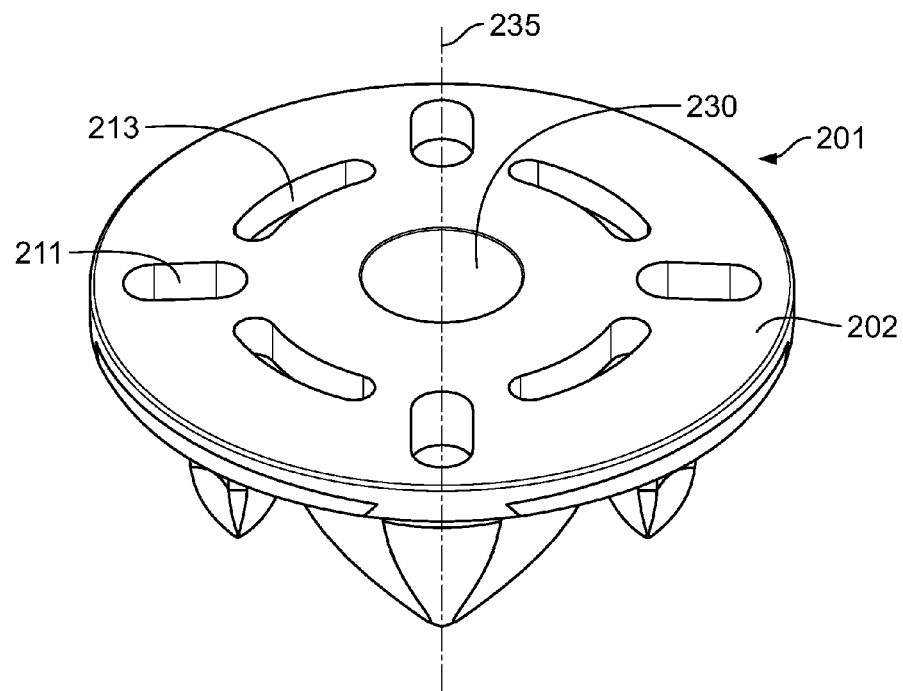
FIG. 6B is a top perspective view of the base of FIG. 6A.
Figure 6C:
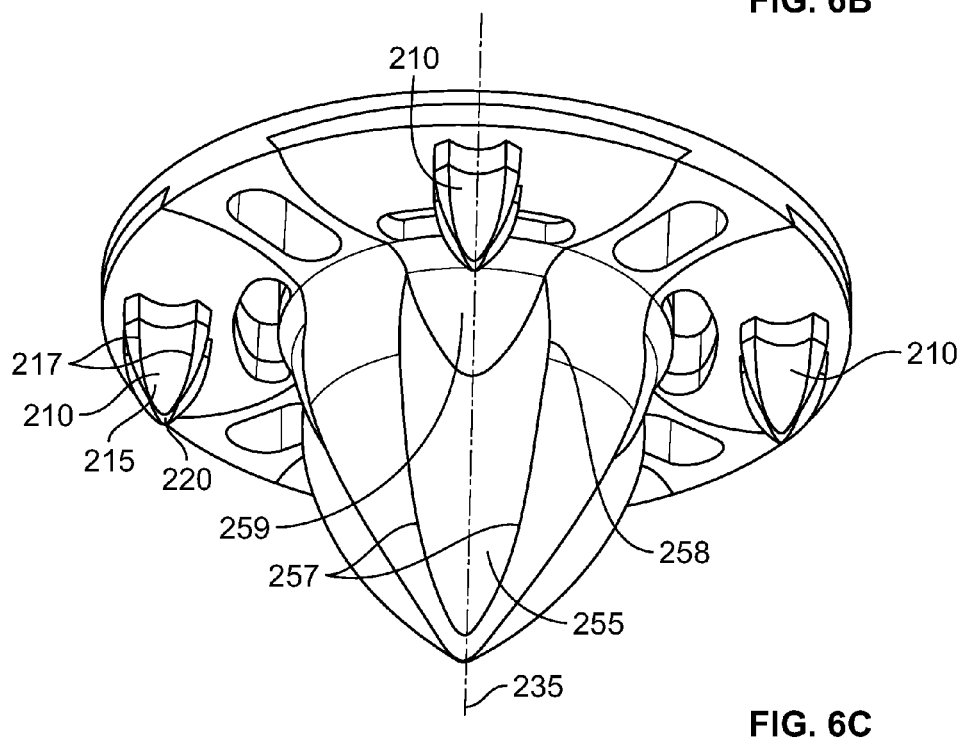
FIG. 6C is another side perspective view of the base of FIG. 6A.

When used as part of a shoulder implant system, anchor 240 may be configured to be driven into the metaphyseal cancellous bone of the humerus and to facilitate engagement between base 200 and the bone for fixation. Anchor 240 may include a plurality of flutes 255 which may extend part or all of the longitudinal length of the anchor, for example from bone-engaging surface 203 to distal tip 275. Each flute 255 may be positioned between two edges 257, with the flute being recessed radially inwardly toward longitudinal axis 235 compared to the edges. Edges 257 may extend radially outwardly from longitudinal axis 235 to varying degrees depending on the position along the longitudinal axis. For example, edges 257 may have a minimum amount of radial extension from longitudinal axis 235 at or near distal tip 275. The distance which the edges 257 extend radially outwardly from longitudinal axis 235 may then increase gradually in the proximal direction toward bone-engaging surface 203. The edges 257 may reach their greatest amount of outward radial extension from longitudinal axis 235 at apex 258. From apex 258 to bone-engaging surface 203, the distance which edges 257 extend radially outward from longitudinal axis 235 may decrease until the edges connect to bone-engaging surface 203. Flutes 255 are preferably concave between two adjacent edges 257. Each flute 255 may include an enhanced fixation surface 259 in the region between bone-engaging surface 203 and a portion of the flute circumferentially aligned with apex 258. The enhanced fixation surface 259 may take the form of a porous metal surface, such as porous titanium alloy, including Tritanium® by Howmedica Osteonics Corporation. As shown in FIG. 6C, fixation surface 259 may be in the general shape of a trough and may be convex. Fixation surfaces 259 may provide for enhanced ingrowth of bone into anchor 240, facilitating better fixation of base 200 following implantation. Fixation surfaces 259 may be rougher than the adjacent surfaces of anchor 240, resulting in greater friction between the fixation surface 259 and the bone. This increased friction may help provide additional fixation by providing additional resistance against pull-out forces.

A fixation ring 238 may surround central anchor 240, the fixation ring extending circumferentially around the central anchor at its connection with bone-engaging surface 203. Fixation ring 238 may generally take the form of a recessed groove. As explained in greater detail below, upon implantation of base 200 into cancellous bone, the bone may flow into fixation ring 238 to help provide additional fixation. As shown in FIG. 6B, fixation surfaces 259 may extend into portions of fixation ring 238 to provide stronger fixation to the bone.

When implanting base 200 into a bone, such as the cancellous bone at the proximal end of the humerus, distal tip 275 of anchor 240 is driven into the bone. Because cancellous bone is relatively soft, the bone may effectively flow along anchor 240, and in particular along the flutes 255 of the anchor. After the apex 258 of the edges 257 passes into the bone, some volume of bone may effectively "spring" back into the areas of flute 255 adjacent enhanced fixation surfaces 259 and also into fixation ring 238. The positioning of the fixation ring 238 in the area of the flutes 255 proximal to the apex 258 results in stronger pull-out resistance for base 200, with the resistance increasing further as bone grows into the pores of fixation surface 259 and fixation ring 238.

Figure 6D:
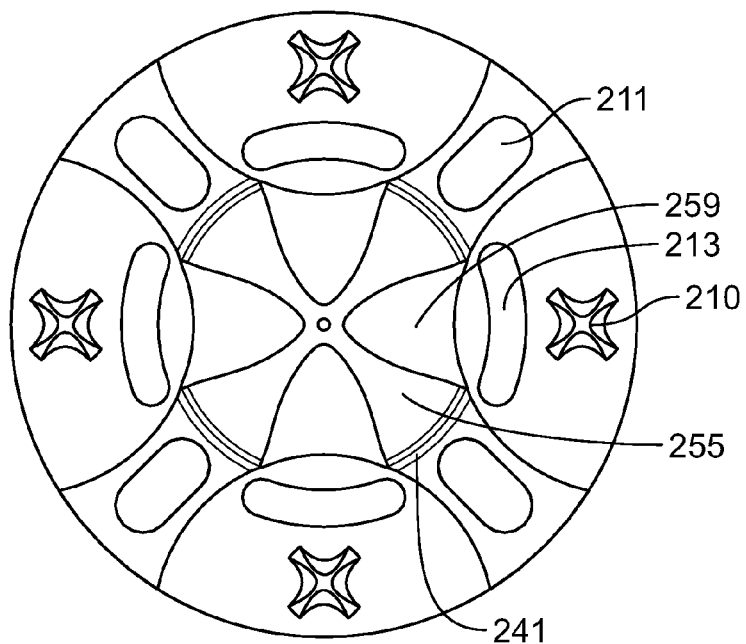
FIG. 6D is a bottom view of the base of FIG. 6A.
Figure 7A:
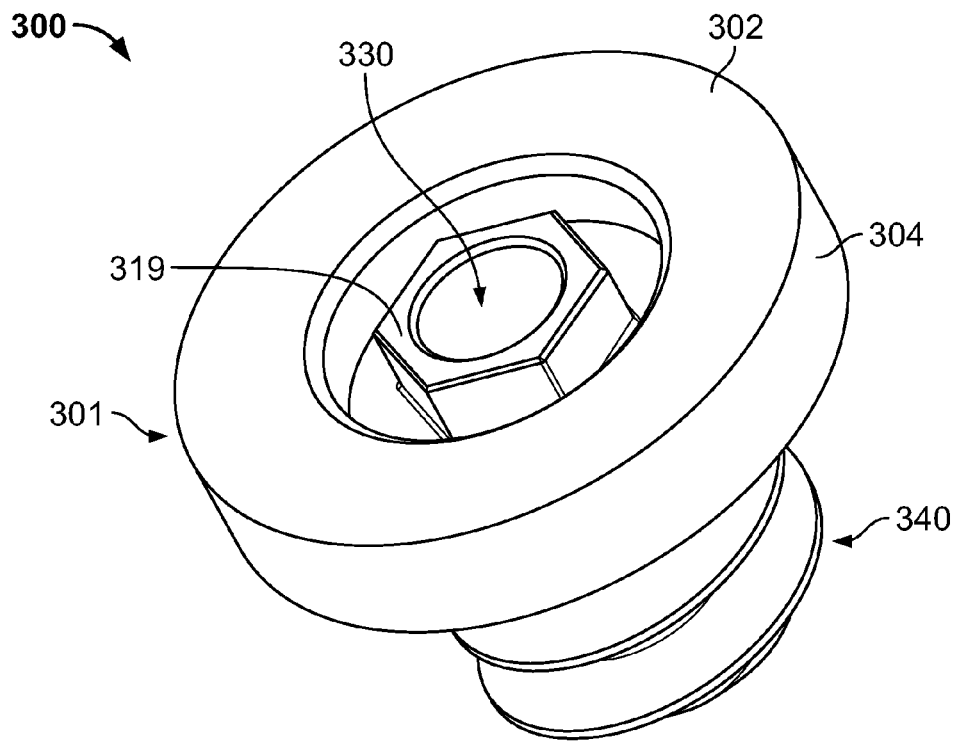
FIG. 7A is a top perspective view of still yet another exemplary stemless prosthesis.
Figure 7B:
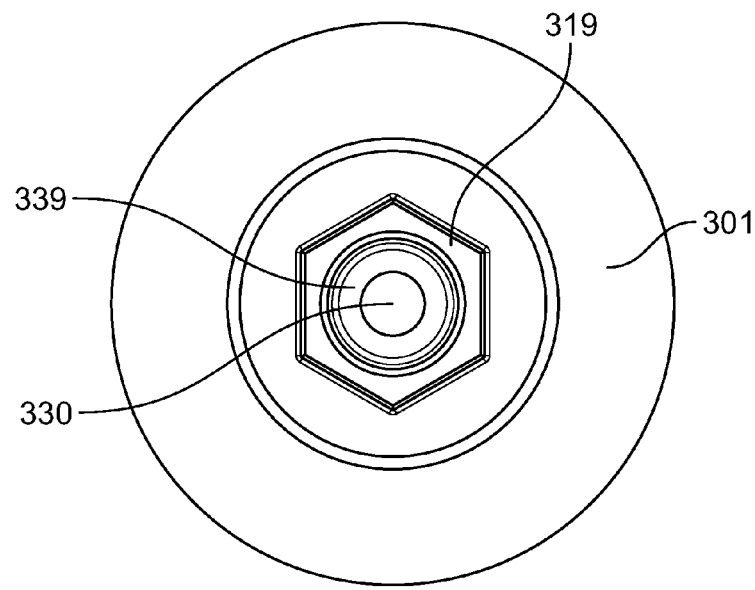
FIG. 7B is a top view of the base of FIG. 7A.
Figure 7C:
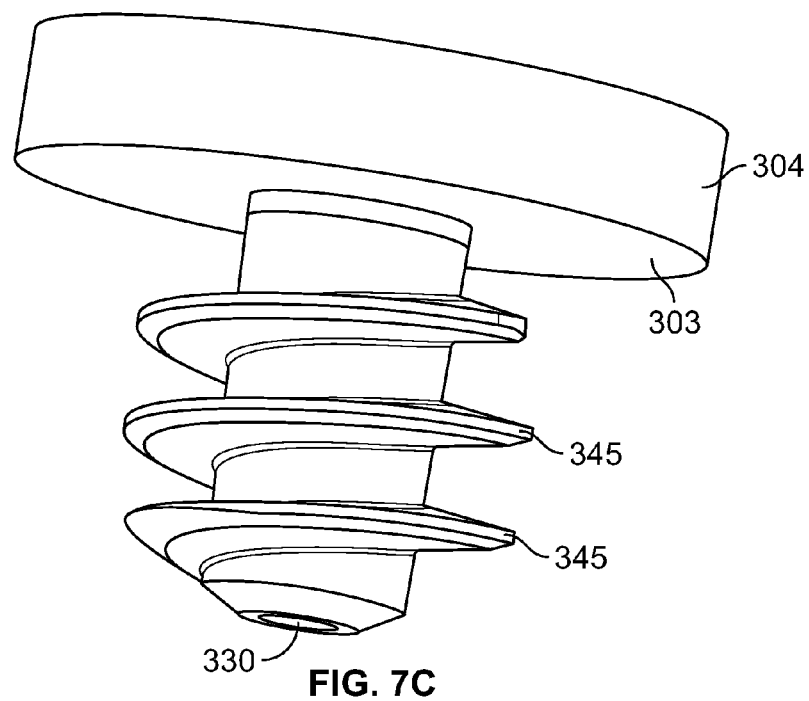
FIG. 7C is a side perspective view of the base of FIG. 7A.
Figure 7D:
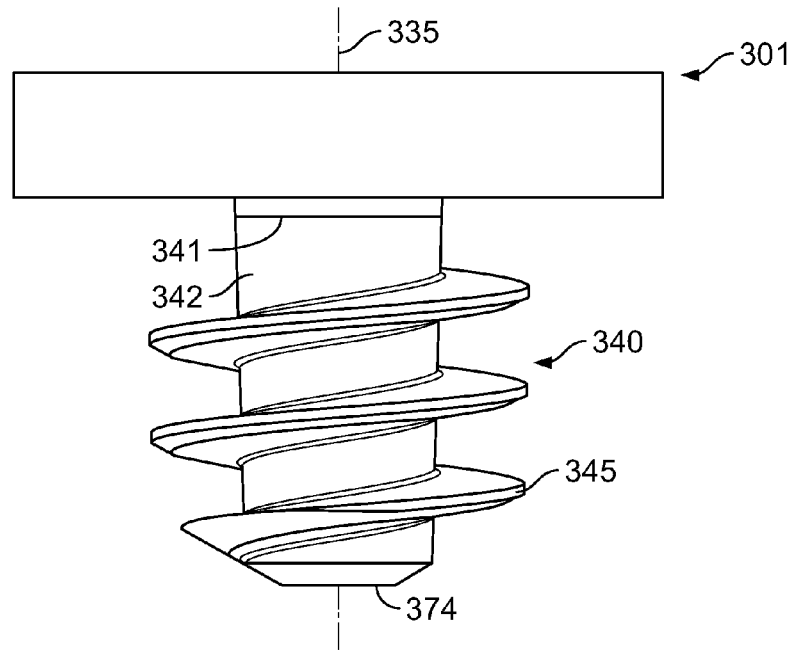
FIG. 7D is a side view of the base of FIG. 7A.

As shown in FIGS. 6C-6D, collar 201 defines a plurality of holes 211 and 213 extending from proximal end surface 202 to bone-engaging surface 203 and includes a plurality of pegs 210 extending distally from bone-engaging surface 203 to distal tips 220. Pegs 210 aid in the fixation of base 200 to the bone, and may particularly assist in initial fixation. While there can be any number of pegs 210 on collar 201, preferably there are four pegs positioned at substantially equal circumferential intervals around the collar. As shown best in 6D, pegs 210 may be located radially outward of holes 213, although other relative spacing between pegs 210 and holes 213 may be appropriate. The use of at least four pegs 210 may provide for enhanced feedback, especially compared to the use of three or fewer pegs, while seating base 200 into the prepared bone during insertion. For example, upon initial contact of pegs 210 with a prepared flat bone surface, the surgeon may be able to easily determine if each of the pegs is simultaneously in contact with the bone. In particular, if all four pegs 210 are in contact with the proximal surface of the bone, the base 200 should not experience any significant amount of rocking or tilting. If the surgeon notices rocking of the base 200, it should be clear that all four pegs 210 are not simultaneously in contact with the bone. If base 200 included three pegs, on the other hand, this rocking motion would not be expected despite a mismatch between a plane defined by the tips of the pegs and a plane of the prepared proximal bone.

As shown in FIG. 6C, pegs 210 extend distally from bone-engaging surface 203 to distal tips 220. Pegs 210 may also include flutes 215. Each flute 215 is positioned between two edges 217, and flutes 215 may be generally concave between the two edges 217. Each peg 210 may have a substantially identical structure to central anchor 240 but scaled to a smaller size. Those structures may provide substantially the same effect as the corresponding features on central anchor 240, although the effects may be less dramatic due to the smaller sizes of the pegs compared to the central anchor. However, in other embodiments, the pegs 210 do not need to have identical but scaled down features as the central anchor 240.

As shown in FIGS. 6B-6D, holes 211 and 213 extend from proximal surface 202 to bone-engaging surface 203. Holes 211 and 213 may be in any shape, round, oval, oblong, etc. In the illustrated embodiment, holes 211 are oblong and a major axis of each hole extends from a point near central anchor 240 radially outwardly toward a point near side flange 204 of collar 201. Holes 213, may also be oblong, and slightly curved so that a major axis of each hole extends in the circumferential direction around central anchor 240. Holes 211 and 213 may have various uses. For example, holes 211 and 213 may be used for passing one or more sutures through to aid in fixation of an object to the base 200. Still further, holes 211 and 213 may be used to engage insertion and/or extraction instrumentation. In the illustrated embodiment, there are four holes 211 and four holes 213, but there may be more or fewer of each of hole 211 and 213. Further, there is no requirement that the number of holes 211 equal the number of holes 213.

In addition to the uses described above, holes 213 may be sized and positioned to facilitate a revision procedure after the base 200 has been implanted into a patient for an amount of time. In the embodiment illustrated in FIG. 6C, holes 213 are positioned adjacent fixation surfaces 259 of flutes 255 and fixation ring 238. With this positioning of holes 213, a surgeon may insert a tool through holes 213 in order to chisel, ream, or otherwise cut away at bone that is adjacent to fixation surface 259 and/or fixation ring 238. Strategically cutting away these areas of bone allows for easier removal of base 200 so that a new device may be implanted in its place.

Each hole 211 may be spaced generally midway between two adjacent pegs 210. However, in some embodiments each hole 211 may be positioned adjacent a corresponding peg 210. In such an embodiment, each hole 211 is preferably disposed adjacent a same side of the associated peg 210. In other words, each hole 211 may be disposed on the right side adjacent to each peg 210, or each hole 211 may be disposed on the left side adjacent to each peg. With each hole 211 adjacent the same side of an associated peg 210, a tool inserted through the holes 211 may be used to ream or cut bone adjacent pegs 210, such that the base 200 may be rotated to move the pegs into the bone cavity adjacent the holes 211. This process may allow for easier removal of base 200 during a revision surgery. Rather than having one hole associated with each peg 210, each peg may include two holes on either side of the peg so that the base 200 may be rotated in either direction to facilitate extraction of the base.

As with base 100', base 200 may further define an opening 230. Opening 230 may extend distally along longitudinal axis 235 from proximal surface 202 of collar 201. Opening 230 may extend partially or fully through anchor 240 along longitudinal axis 235 or it may be shallow and extend only into collar 201. A humeral head component (not shown) may be placed within opening 230 and attached thereto, for example by a taper lock such as a Morse taper. The humeral head component may be attached by any known securement means including screw or friction fit.

It should be understood that bases 100' and 200 may be formed of any suitable prosthetic grade material, including, for example, titanium alloys and/or other biocompatible metals and metal alloys. In some embodiments of base 200, the porous portions of the base, such as fixation surface 259 and fixation ring 238, may be provided via additive manufacturing over a base material such as titanium alloy. Further, although holes 211 and 213 are only described in connection with base 200, similar or identical holes may be provided in base 100. Still further, base 100 may include surfaces similar to fixation surfaces 259 and fixation ring 238, for substantially the same purpose of increased fixation.

FIGS. 7A-7D show base 300 of a stemless prosthesis according to another embodiment of disclosure. Base 300 generally includes collar 301 coupled with central anchor 340. Collar 301 may be generally cylindrical or annular and includes a proximal end surface 302, a distal bone engaging-surface 303, and a side flange surface 304. Proximal end surface 302 may be flat as shown, but in other embodiments it may be inclined or sloped. Side flange surface 304 may have a uniform height, the height measured from distal to proximal ends of side flange surface 304, or the height may vary along proximal end surface 302. Although shown as generally cylindrical or annular, collar 301 may have other shapes.

Base 300 includes central anchor 340 coupled to collar 301 at a first end 341 and extending distally from the collar along a longitudinal axis 335 to a second end 374. In the illustrated embodiment, anchor 340 is slightly tapered along longitudinal axis 335 so that first end 341 has a relatively larger diameter, with the diameter of the anchor slightly narrowing toward second end 374; although, in some embodiments, anchor 340 may be of uniform size and not tapered.

Base 300 includes a socket, which in the illustrated embodiment is a hex member 319, positioned within an interior cavity of collar 301. Hex member 319 defines an opening 330 which is adapted to receive an articulating component (not shown) of the stemless implant. In the illustrated embodiment, opening 330 extends from proximal end surface 302 of collar 301 along longitudinal axis 335 to annular proximal surface 339 of anchor 340, where the diameter of the opening decreases. With the decreased diameter, opening 330 then extends from annular proximal surface 339 of anchor 340 along longitudinal axis 335 to second end 374. Thus, anchor 340 of base 300 may be cannulated. In this way, base 300 may be inserted through a pilot wire, such as a K-wire, to help provide more accurate placement of base member 300 within a prepared portion of the bone. As illustrated, hex member 319 has a hexagonal shape. The proximal end of hex member 319 may be substantially flush with the proximal surface 302 of collar 301, although in some embodiments it may extend either proximally or distally of proximal surface 302. A driver (not shown) having a mating internal hex member may engage hex member 319. This may cause rotation of hex member 319 and base 300 which may provide torque for fixation of base member 300 in the bone. It should be understood that although the socket is illustrated as having a hexagonal shape, any shape suitable for transmitting torque from a correspondingly shaped driver tool may be suitable.

Anchor 340 includes outer wall 342 extending from first end 341 toward second end 374. When used as part of a shoulder implant system, anchor 340 may be configured to be driven into the metaphyseal cancellous bone of the humerus and to facilitate engagement between base 300 and the bone for fixation. Threads 345 extend around outer wall 342 of anchor 340 and may be disposed helically in a screw-like configuration. When the driver (not shown) engages hex member 319 and causes rotation of base 300, threads 345 may engage the bone and may provide greater fixation of the base to the bone.

Figure 8A:
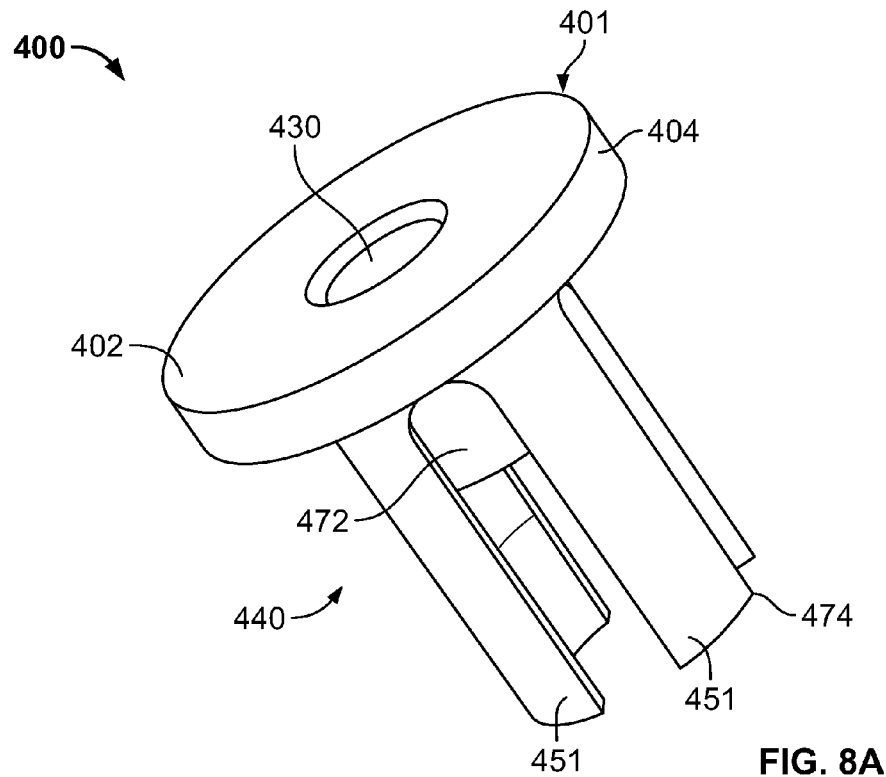
FIG. 8A is a top perspective view of still yet another exemplary stemless prosthesis.
Figure 8B:
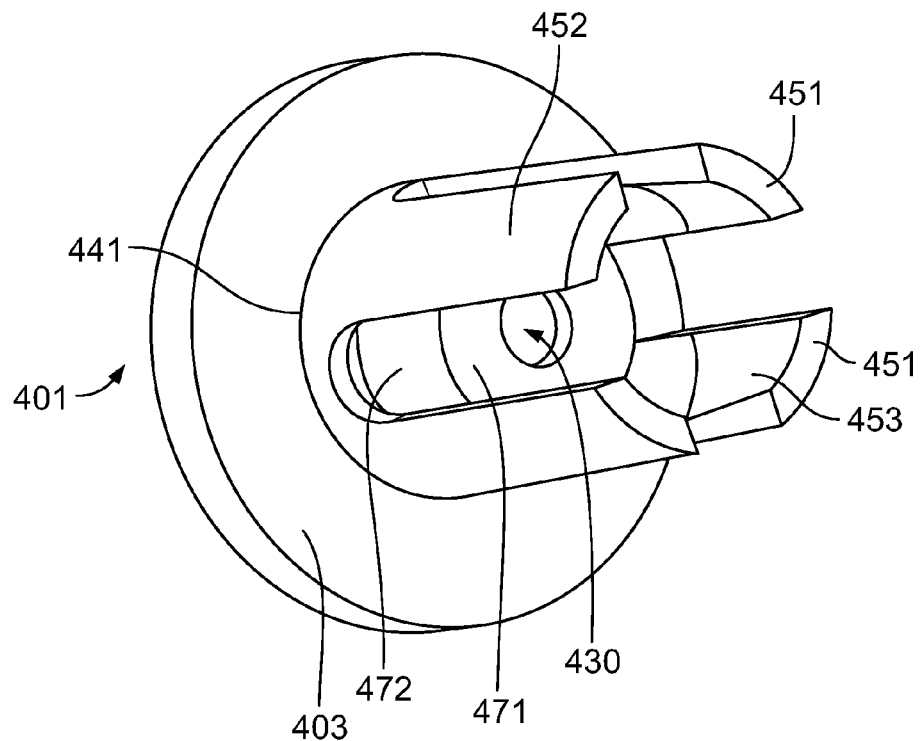
FIG. 8B is a bottom perspective view of the base of FIG. 8A.
Figure 8C:
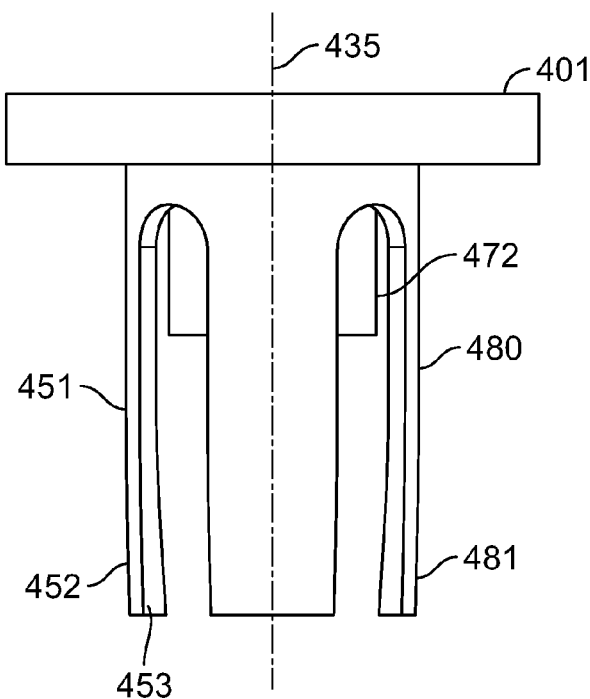
FIG. 8C is a side view of the base of FIG. 8A.

FIGS. 8A-8C show base 400 of a stemless prosthesis according to another embodiment of disclosure. Base 400 generally includes collar 401 coupled with central anchor 440. Collar 401 may be generally cylindrical or annular and includes a proximal end surface 402, a distal bone engaging-surface 403, and a side flange surface 404. Proximal end surface 402 may be flat as shown, but in other embodiments it may be inclined or sloped. Side flange surface 404 may have a uniform height, the height measured from distal to proximal ends of side flange surface 404, or the height may vary along proximal end surface 402. Collar 401 may have other shapes, such as generally oblong and may include additional holes for use with insertion/extraction tools and/or for accepting sutures, similar to holes described in embodiments above.

Base 400 includes central anchor 440 coupled to collar 401 at a first end 441 and extending distally from the collar along a longitudinal axis 435 to a second end 474. As illustrated, anchor 440 may include flanges 451 extending from bone-engaging surface 403, substantially parallel to longitudinal axis 435, to second end 474 of the anchor. As shown in FIGS. 15 and 16, flanges 451 may include outer surfaces 452 and inner surfaces 453. Inner surfaces 453 may be slightly concave along at least a portion of the inner surfaces. Inner surfaces 453 may include internal threads along at least a portion thereof. Flanges 451 may include a straight portion 480 and a tapered portion 481. Straight portion 480 may extend generally parallel to longitudinal axis 435, whereas tapered portion 481 may taper radially inwardly from the distal end of straight portion 480 to second end 474 of anchor 440 such that inner surfaces 453 nearer second end 474 may be radially closer to longitudinal axis 435 than a point on inner surface nearer straight portion 480. Likewise, outer surfaces 452 nearer second end 474 may be radially closer to longitudinal axis 435 than a point on the outer surface nearer straight portion 480. However, the degree of the taper of the outer surfaces 452 and inner surfaces 453 of flanges 451 may be different. For example, the taper of outer surfaces 452 may be less than the taper of the inner surfaces.

Anchor 440 includes support 472, which may be a cylinder, extending from bone-engaging surface 403 of collar 401 along longitudinal axis 435 to a distal end surface 471 of the cylinder. Support 472 may be positioned generally centrally on bone-engaging surface 403.

Base 400 includes opening 430 extending from proximal end surface 402 of collar 401 along longitudinal axis 435 to a distal end surface 471 of support 472. The diameter of opening 430 may decrease near the distal end of support 472. In the illustrated example, base 400 may be adapted to couple to a proximal humerus of a patient, with a prosthetic humeral head adapted to couple to the base via opening 430, the prosthetic humeral head intended to articulate with a native or prosthetic glenoid of the shoulder joint. Although opening 430 may have any shape that suitably mates with the corresponding portion of the prosthetic humeral head, in one example a taper such as a Morse taper may be used to lock the prosthetic humeral head within opening 430.

The outer or proximal end surface 102 of stemless implant 100, for example has a plurality of apertures or surface features 120 about a circumference thereof. These apertures or surface features 120 define an inner central portion 140 of stemless implant 100 that is configured to be removed therefrom if a revision procedure is performed. Surface features 120 act as a guide in removal of central portion 140 defined by the inside of dashed circle 125. In reference to stemless implant 100', inner circumference of collar 101' defines an inner central portion that is configured to be removed therefrom if a revision procedure is performed. The inner central portion encompasses the structure of and adjacent to elements 115', 119', 130' and 139' shown in FIG. 5C, for example. In reference to stemless implant 200, apertures or holes 211, 213 define an inner central portion similar to that of inner central portion 140 of stemless implant 100 which is inner circumference of collar 101' defines an inner central portion that is configured to be removed therefrom if a revision procedure is performed. The holes 211, 213 act as a guide in removal of the central portion of implant 200. In reference to stemless implant 300, an inner wall extending downwardly and perpendicularly to proximal end surface 302 defines an inner central portion that is configured to be removed therefrom if a revision procedure is performed. The inner central portion encompasses the structure of and adjacent to elements 319, 339, 330 shown in FIG. 7B, for example, including the complete removal of central anchor 340. In reference to stemless implant 400, an inner wall extending downwardly and perpendicularly to proximal end surface 402 defines an inner central portion that is configured to be removed therefrom if a revision procedure is performed. The inner central portion encompasses the structure adjacent to the inner central portion including, for example, a portion of the proximal end surface 402. The removal of a portion of stemless implant 400 in a revision procedure may include some or all of central anchor 440.

Figure 9:
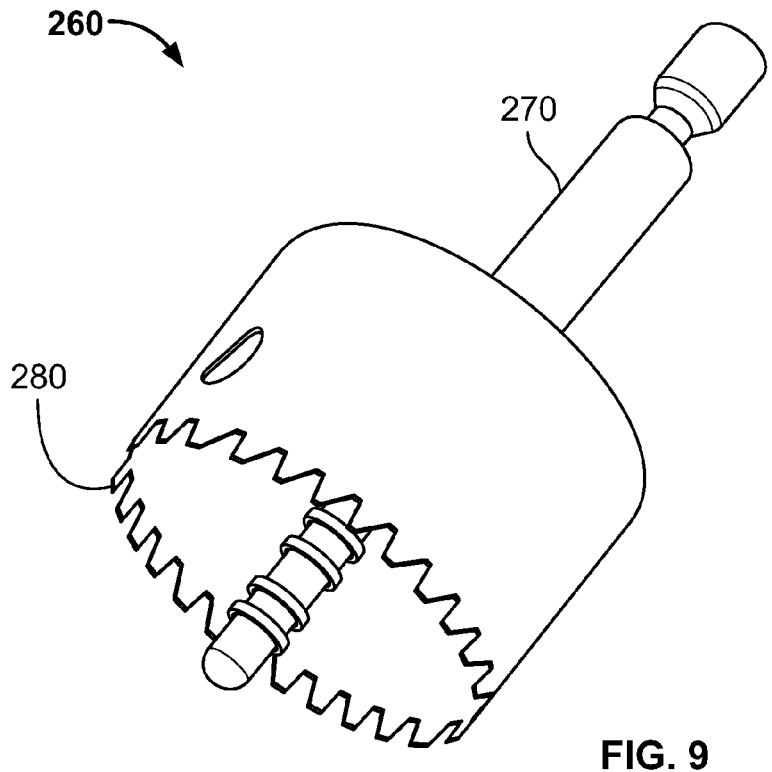
FIG. 9 is an exemplary cutting instrument that can be used to separate or disconnect a central portion of the stemless prosthesis shown in FIG. 3, for example.
Figure 10:
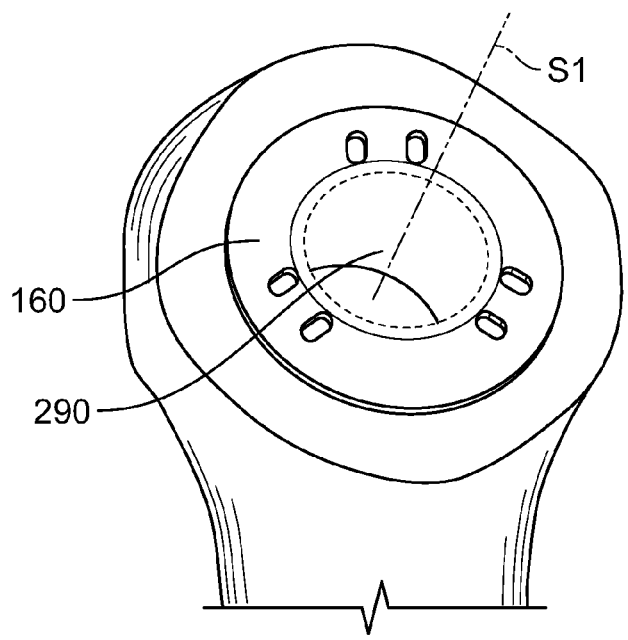
FIG. 10 is a perspective view of the stemless prosthesis shown in FIG. 4 with the central portion thereof having been removed therefrom.

In a primary procedure, apertures 150, 130', 230, 330, 430 of stemless implants 100, 100', 200, 300, 400 respectively, may receive a protrusion of another component of a shoulder arthroplasty system. In order to convert stemless implant 100, 100', 200, 300, 400 in a revision procedure, a cutting device or burr 260 as shown in FIG. 9, is used to reference features 120 and dashed circle 125 of stemless implant 100, for example, to position burr 260 in contact with outer surface 102. Burr 260 is then moved distally in order to disconnect the central portion 140 of stemless implant 100, for example, and to create a hole 290 sufficient to receive at least a portion of a humeral stem along stem axis S1 as shown in FIG. 10. After central portion 140 is disconnected from stemless implant 100, a collar portion 160 is created. The respective inner central portions of stemless implants 100', 200, 300 and 400 can be removed in a similar manner as to that described with respect to implant 100.

Burr 260 includes a centering pin 270 adapted to be received in a central aperture 150 of central portion 140 as well as a serrated cutting surface 280 adapted to contact and cut through solid portions of stemless implant 100 between apertures 120 or through surface features 120.

Figure 11:
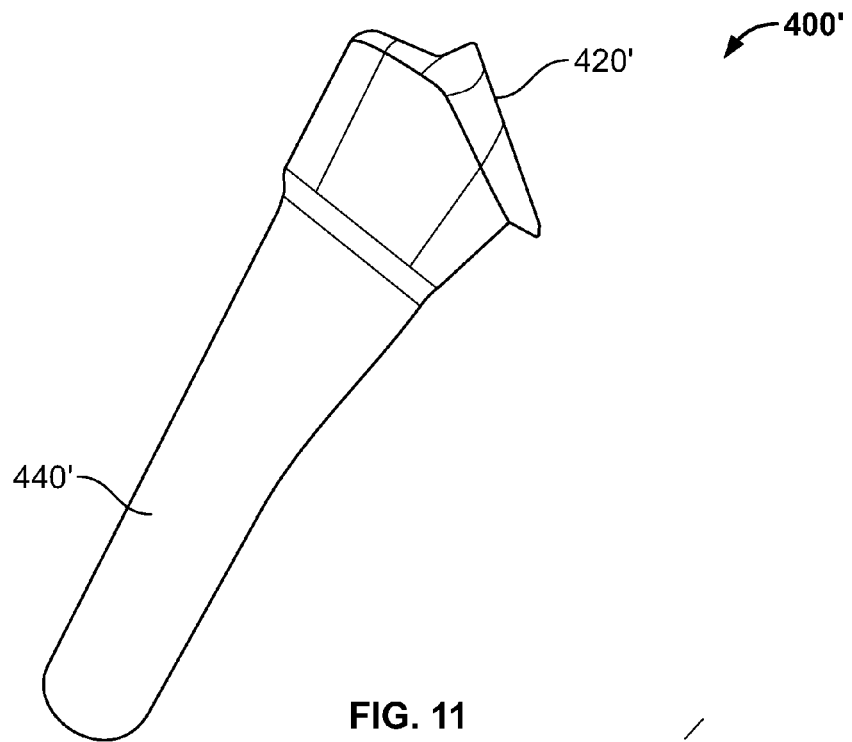
FIG. 11 is a perspective view of an exemplary shoulder stem.

FIG. 10 shows collar portion 160 adjacent resection line 30 of humerus 12. With central portion 140 of stemless implant 100 now removed, a central hole 290 is created for receipt of a shoulder stem 400' as shown in FIG. 11. Shoulder stem 400' includes an engagement portion 420' for receipt of a humeral head or other components of a total shoulder arthroplasty system not shown. Shoulder stem 400' includes a shaft portion 440' that is inserted through central hole 290 and into contact with bone in the canal of the humerus.

Figure 12A:
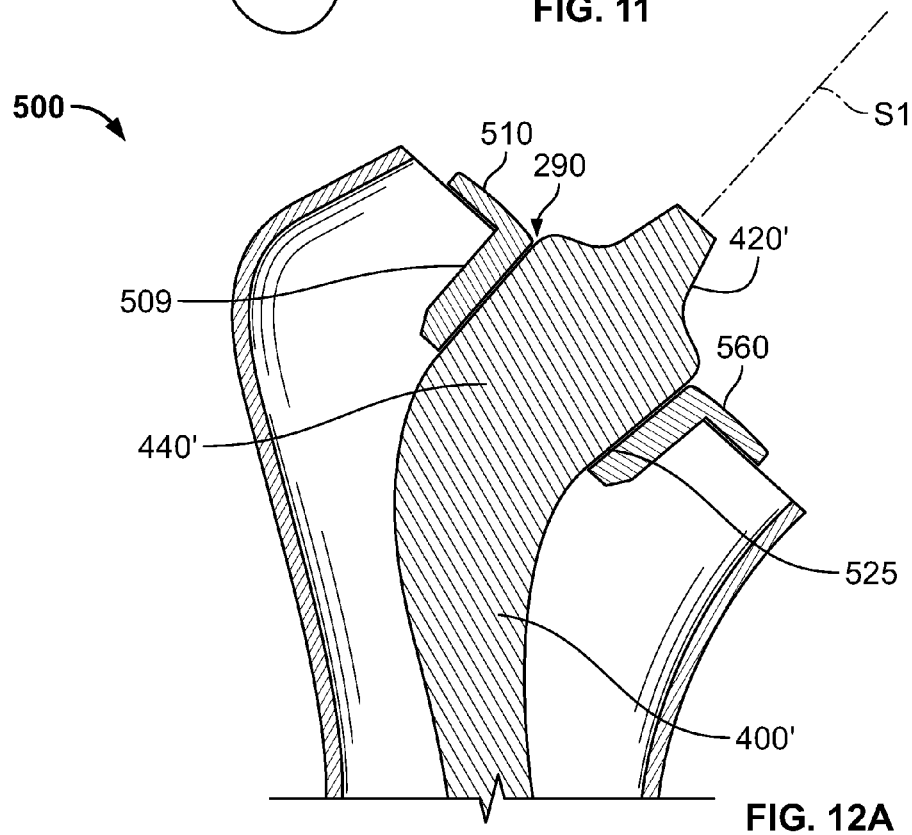
FIG. 12a is a cross-sectional view of a cored out stemless prosthesis of the present invention with a shoulder stem inserted at least partially through its center, the shoulder stem having a trunnion.

One embodiment of an orthopedic revision system 500 is shown in FIG. 12A. System 500 includes a converted stemless implant or base member 510 having a collar portion 560 and at least one stabilization portion 509 extending outwardly or distally from collar portion 560. System 500 further includes stem member 400' in which shaft portion 440' is configured to be received at least partially through a central hole or opening 290 in collar portion 560 such that attachment portion 420' lies adjacent collar portion 560 and at least a portion of shaft portion 440' lies adjacent at least one stabilizing portion 509. Based on the size and movement of burr 260 with respect to the stemless implant shown in FIG. 12A, collar portion 560 and at least one stabilization portion 509 of base member 510 may form an open cylindrical shaft 525.

Collar portion 560 extends in a direction transverse to at least one stabilization portion 509. The collar portion 560 and the at least one stabilization portion 509 intersect to define a corner 515 adapted to lie adjacent to an edge of a medullary canal of a patient's bone. Base member 510 has an initial configuration and a revision configuration. In the initial configuration, collar portion 560 is closed such as shown in stemless implant 100 in FIG. 4 for example, and in the revision configuration defines central hole 290 as shown in FIG. 10 for example.

Figure 12B:
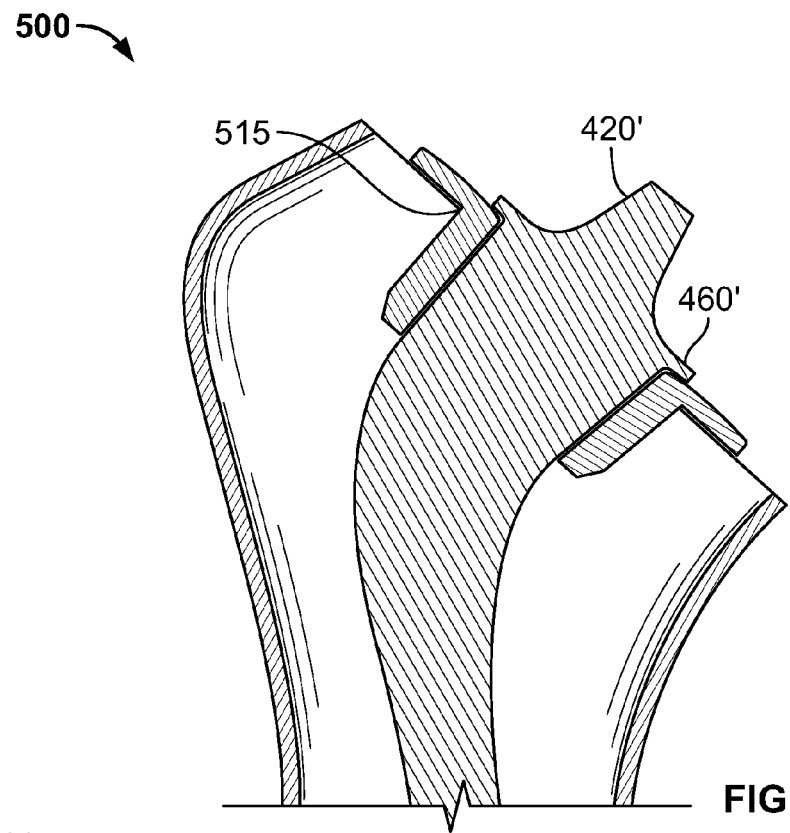
FIG. 12b is a cross-sectional view of a cored out stemless prosthesis of the present invention with a shoulder stem having a flange for contacting an outer surface of the stemless prosthesis to position the shoulder stem with respect to the stemless prosthesis.
Figure 13:
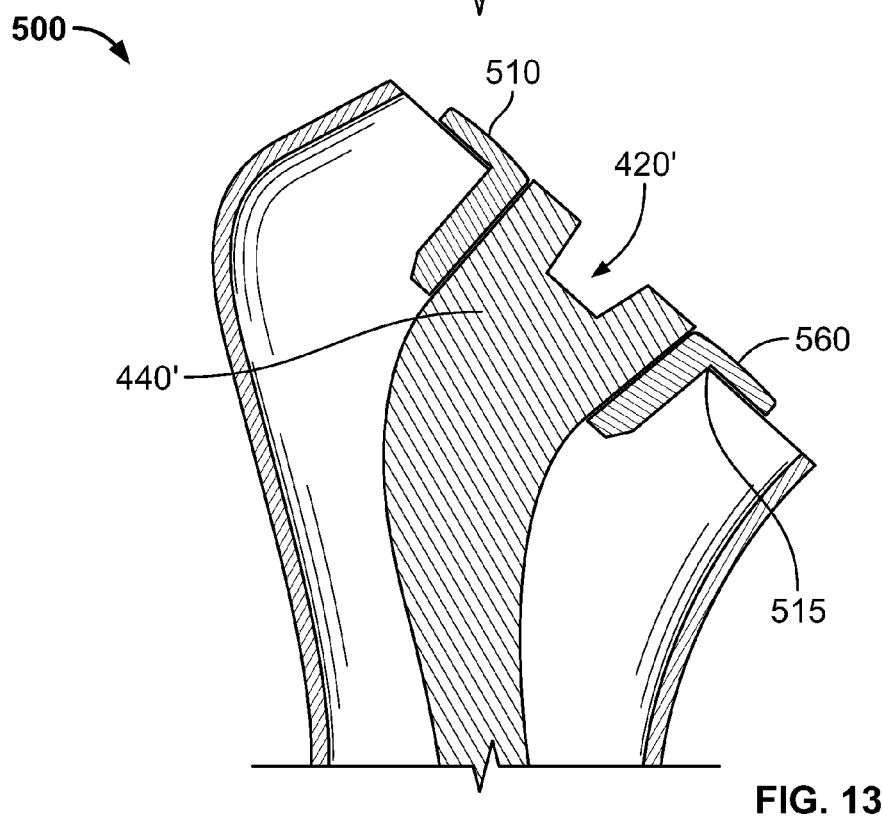
FIG. 13 is a cross-sectional view of a cored out stemless prosthesis of the present invention with another embodiment of a shoulder stem inserted at least partially through its center, the shoulder stem having a recess.

In another embodiment, stem member 400' includes a ledge portion 460' configured to contact and lay adjacent to collar portion 560 of base member 510 as shown in FIG. 12A when stem member 400' is operatively coupled to base member 510. Attachment portion 420' of stem member 400' is a trunnion, as shown in FIG. 12B, for insertion into a recess of an articulation member (not shown) to operatively couple stem member 400' to the articulation member. In FIG. 13, attachment portion 420' defines a recess for receipt of an engagement portion of an articulation member (not shown) to operatively couple the stem member to the articulation member.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic revision system comprising:
a base member having a collar portion and at least one stabilization portion extending distally from the collar portion; and
a stem member having an attachment portion and a shaft portion,
wherein the stem member is configured to be received at least partially through an opening in the collar portion such that the attachment portion lies adjacent the collar portion and the shaft portion lies adjacent the at least one stabilizing portion.

2. The orthopedic revision system of claim 1, wherein the collar portion and the at least one stabilization portion of the base member include open cylindrical shafts.

3. The orthopedic revision system of claim 1, wherein the collar portion extends in a direction transverse to the at least one stabilization portion.

4. The orthopedic revision system of claim 3, wherein the collar portion and the at least one stabilization portion intersect to define a corner adapted to lie adjacent to an edge of a medullary canal of a patient's bone.

5. The orthopedic revision system of claim 1, wherein the base member has an initial configuration and a revision configuration, the collar portion being closed in the initial configuration and defining an opening in the revision configuration.

6. The orthopedic revision system of claim 5, wherein an inner portion of the collar portion is removed to convert the collar portion from the initial configuration to the revision configuration.

7. The orthopedic revision system of claim 1, wherein the stem member includes a ledge portion configured to contact and lay adjacent to the collar portion of the base member when the stem member is operatively coupled to the base member.

8. The orthopedic revision system of claim 1, wherein the attachment portion of the stem member defines an engagement portion for insertion into a recess of an articulation member to operatively couple the stem member to the articulation member.

9. The orthopedic revision system of claim 1, wherein the attachment portion defines a recess for receipt of an engagement portion of an articulation member to operatively couple the stem member to the articulation member.

10. An orthopedic revision system comprising:
a base member having a revision configuration including a collar portion and at least one stabilization portion extending distally from the collar portion in a direction transverse from the collar portion; and
a stem member having an attachment portion and a shaft portion,
wherein the stem member is configured to be received at least partially through an opening in the collar portion such that the attachment portion lies adjacent the collar portion and the shaft portion lies adjacent the at least one stabilizing portion.

11. The orthopedic revision system of claim 10, wherein the collar portion and the at least one stabilization portion of the base member include open cylindrical shafts.

12. The orthopedic revision system of claim 10, wherein the collar portion extends in a direction transverse to the at least one stabilization portion.

13. The orthopedic revision system of claim 12, wherein the collar portion and the at least one stabilization portion intersect to define a corner adapted to lie adjacent to an edge of a medullary canal of a patient's bone.

14. The orthopedic revision system of claim 10, wherein the base member has an initial configuration and the revision configuration, the collar portion being closed in the initial configuration and defining the opening in the revision configuration.

15. The orthopedic revision system of claim 14, wherein an inner portion of the collar portion is removed to convert the collar portion from the initial configuration to the revision configuration.

16. The orthopedic revision system of claim 10, wherein the stem member includes a ledge portion configured to contact and lay adjacent to the collar portion of the base member when the stem member is operatively coupled to the base member.

17. The orthopedic revision system of claim 10, wherein the attachment portion of the stem member defines an engagement portion for insertion into a recess of an articulation member to operatively couple the stem member to the articulation member.

18. The orthopedic revision system of claim 10, wherein the attachment portion defines a recess for receipt of an engagement portion of an articulation member to operatively couple the stem member to the articulation member.

\* \* \* \* \*